United States Patent [19]

Flaherty et al.

[11] 4,351,031
[45] Sep. 21, 1982

[54] NONDESTRUCTIVE TESTING SYSTEM HAVING AUTOMATIC SET-UP MEANS

[75] Inventors: John J. Flaherty, Elk Grove Village; Eric J. Strauts, Park Ridge; Helmut F. Wagerer, Des Plaines; Timothy C. Loose, Chicago, all of Ill.

[73] Assignee: Magnaflux Corporation, Chicago, Ill.

[21] Appl. No.: 204,946

[22] Filed: Nov. 7, 1980

[51] Int. Cl.³ .............................................. G01R 33/00
[52] U.S. Cl. .................................... 364/580; 324/238
[58] Field of Search ............... 364/580, 579, 507, 550, 364/483, 481, 20; 324/238

[56] References Cited

U.S. PATENT DOCUMENTS

| | | | |
|---|---|---|---|
| 2,939,073 | 5/1960 | Eul, Jr. .................................. | 324/238 |
| 4,207,520 | 6/1980 | Flora et al. ........................... | 324/238 |
| 4,213,183 | 7/1980 | Barron et al. ........................ | 364/507 |
| 4,247,818 | 1/1981 | Hiroshima ....................... | 324/238 X |
| 4,255,792 | 3/1981 | Das ...................................... | 364/580 |
| 4,261,041 | 4/1981 | Starr ................................ | 364/580 X |
| 4,270,178 | 5/1981 | Lillig .................................... | 364/579 |
| 4,271,515 | 6/1981 | Axtell et al. .................... | 364/580 X |
| 4,280,220 | 7/1981 | Vaeches ........................ | 364/580 X |

Primary Examiner—Edward J. Wise
Attorney, Agent, or Firm—Neuman, Williams, Anderson & Olson

[57] ABSTRACT

An eddy current type of nondestructive testing instrument is disclosed in which the operating frequency is automatically adjusted in accordance with a comparison of output signals obtained in scanning operations in which the frequency is adjusted over its range. The system may be used, for example, in providing lift-off compensation for conductivity measurements or flaw detection or it may be used for sorting of parts of different characteristics.

14 Claims, 12 Drawing Figures

NONDESTRUCTIVE TESTING SYSTEM HAVING AUTOMATIC SET-UP MEANS

This invention relates to a nondestructive testing system and more particularly to a nondestructive testing system which incorporates an automatic set-up means operable to obtain optimum results under a variety of test conditions. The system is readily operable and a minimum amount of time is required for adjustment of the instrument prior to initiating a testing operation. At the same time, the system is highly reliable, produces very accurate results and it is comparatively simple and economically manufacturable.

BACKGROUND OF THE INVENTION

Nondestructive testing systems of the prior art have been capable of achieving very accurate and reliable results when properly adjusted. However, the required adjustment procedures usually have a certain degree of complexity and when an operator is unskilled or inattentive or has not taken enough time to read instruction manuals and learn proper procedures, the results obtained may be inaccurate or unreliable. As a result, defective products have sometimes been passed as being without any defect, sometimes with very expensive results. In some cases, a safety hazard may result.

SUMMARY OF THE INVENTION

This invention was evolved with the general object of overcoming disadvantages of prior nondestructive testing systems and of providing a system which can be easily and quickly set up for accurate and reliable results.

The invention is illustrated herein as applied to an eddy current type of nondestructive testing instrument and more particularly to an instrument for measuring conductivity, of a type as disclosed in U.S. Pat. No. 2,939,073 issued May 31, 1960 to Edward A. Eul, Jr. An important application for such instruments is the detection of cracks or the like which produce changes in the effective conductivity. In a conductivity measuring or flow detection instrument as disclosed in the Eul patent, the output signal obtained is desirably substantially independent of variations in spacing or dimensional relationships between a test coil and the structure being tested. To set up the instrument, the operating frequency is adjusted to a value defined by an intersection between two curves, one curve being a plot of voltage versus frequency with the test coil against a test piece and the other curve being a plot of voltage versus frequency with the coil spaced from the test piece. By operating at that frequency, the instrument is highly sensitive to changes in conductivity and thereby to cracks or other flaws while being comparatively insensitive to changes in the spacing between the test coil and the part in a test. Thus, a lift-off compensation is attained. Very accurate results can be attained with proper adjustment but such adjustment is somewhat difficult and is also time-consuming.

In a system constructed in accordance with this invention, memory means and the value of a test parameter are controlled by program means under each of a plurality of different set-up test conditions. The memory means stores the values of output signals and concurrent values of the test parameter such as the operating frequency of an eddy current instrument. After the values of a plurality of sets of signals obtained during such test conditions are stored, they are compared and an optimum parameter value is established and stored which corresponds to a predetermined correspondence between output signals during the different test conditions. The set-up means then operates to adjust the parameter to the stored optimum value for subsequent testing of test structures of unknown characteristics.

The arrangement of the invention may be utilized in conjunction with an instrument as disclosed in the Eul patent to adjust the operating frequency to obtain lift-off compensation, for subsequent measurement of conductivity and for detection of flaws which affect the measured conductivity of a part. Alternatively, the system of the invention might be used to adjust the operating frequency to obtain maximum sensitivity to changes in spacing or other changes in dimensional relationships between a test coil and a test structure, while at the same time minimizing the effects of variations in the conductivity of the test structure.

In another mode of operation, the arrangement may be used for facilitating sorting of parts of different characteristics. In this mode of operation, one of the set-up test conditions is established by testing one type of part and another test condition is established by testing a second type of part. After varying the test parameter over a certain range and storing of the output signals obtained, a value of the parameter may be established at which there is a maximum difference between the output signals obtained while testing the parts of different characteristics. Then a sorting operation may be performed in which a high degree of discrimination is obtained between the two different types of parts.

Important features of the invention relate to the adaptation of the circuitry of a nondestructive testing system for performance of the automatic set-up operations.

Additional features of the invention relate to the manner in which data is obtained and stored for use in the set-up operations. A specific feature is in an automatic balancing operation involving the incrementing and decrementing of signals produced by one or more digital-to-analog converters until a trigger level is established. The balancing operation is also used for the purpose of determining the level of a signal produced from the nondestructive testing instrumentation, such as from the output of a bridge circuit connected to an eddy current probe. By determining the change in level required to obtain a balance, data is obtained as to the level of the output signal of the nondestructive testing circuitry.

This invention contemplates other objects, features and advantages which will become more fully apparent from the following detailed description taken in conjunction with the accompanying drawings.

DESCRIPTION OF A PREFERRED EMBODIMENT

Figure 1:
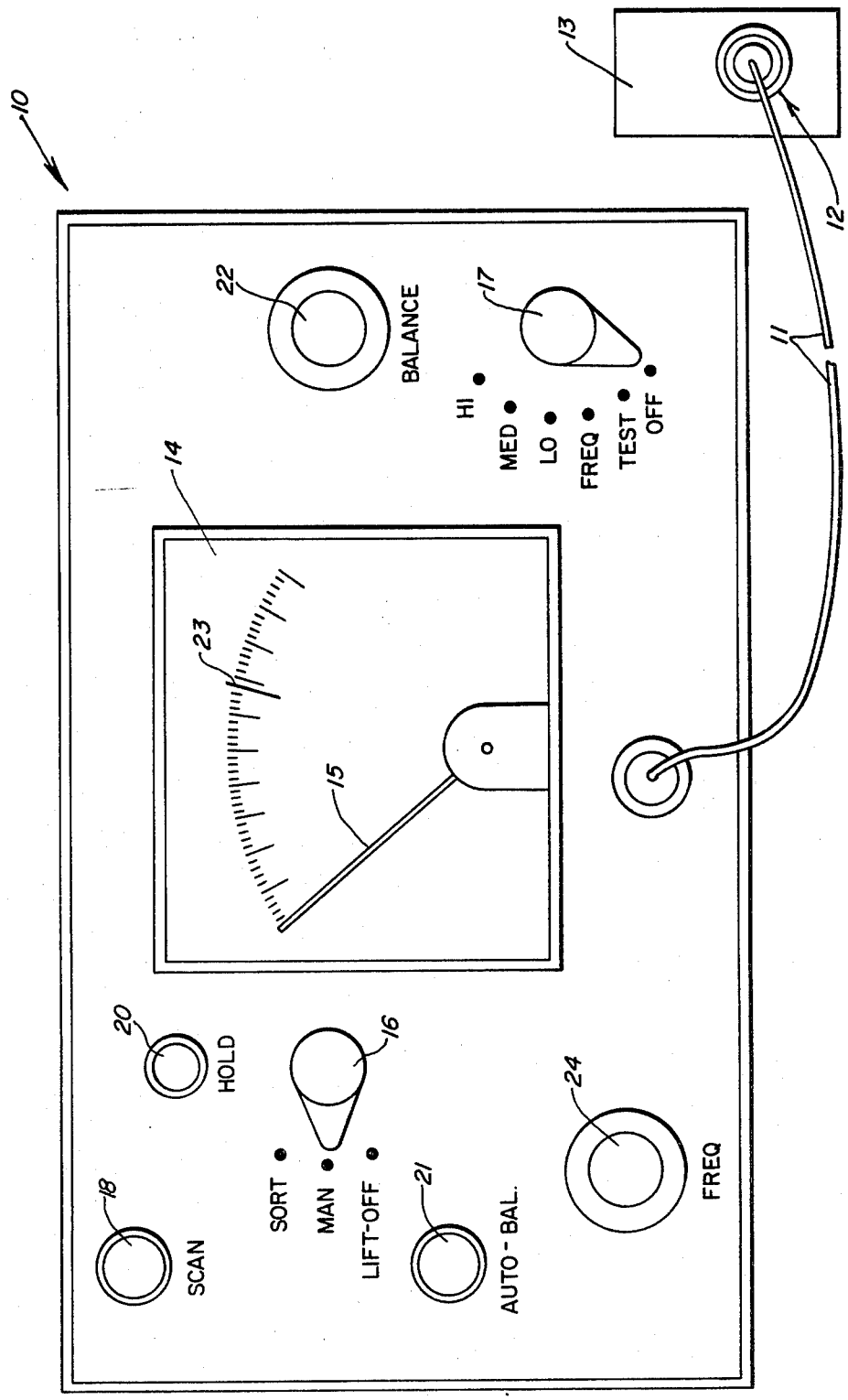
FIG. 1 is a plan view of an eddy current instrument which incorporates an automatic set-up means according to the invention.

Reference numeral 10 generally designates an eddy current instrument which includes automatic set-up controls and circuitry constructed in accordance with the principles of this invention.

The illustrated instrument 10 is designed for the measurement of electrical conductivity and the detection of cracks or other flaws which change the effective conductivity and also for sorting of parts having different electrical conductivities. In the operation of the instrument, it is connected through a cable 11 to a probe 12 which may be placed against the surface of a part 13 and the conductivity of the part 13 may then be read on the scale of a meter 14 having a pointer 15.

Prior to use of the instrument 10 in measuring conductivity, a lift-off compensation procedure should be followed for the purpose of rendering the measurements insensitive to variations in the spacing between the probe 12 and the surface of the part 13. Such variations in spacing may be caused by surface coatings, roughness, oxides, scales and rocking or wobbling of the probe during testing. In prior art instruments, the lift-off compensation has been performed manually and is somewhat complicated, involving repeated adjustments and readjustments of frequency and balance controls. With the automatic set-up means of this invention, however, the lift-off compensation procedure is quite simple. In particular, a control knob 16 is placed in a lift-off position as illustrated and, with a mode control knob 17 in either a "LO", "MED" or "HI" position, a scan button 18 is depressed while placing the probe 12 against the part 13, holding a shim of paper between the end of the probe 12 and the surface of the part 13. A "HOLD" signal light 20 is then energized for a short time and after it is deenergized, the operation is repeated but with the shim removed and with the end of the probe 12 against the surface of the part 13, the scan button being again depressed. The hold signal light 20 is then again energized for a short time, then becomes deenergized and is then reenergized for a short time interval to effect a blinking operation, indicating that the instrument has been properly adjusted for lift-off.

An automatic balancing operation is automatically performed as part of the lift-off compensation operation and also as part of a sorting set-up operation. However, the automatic balancing operation may be performed at any time by depression of a balance control button 21. It may also be performed manually by using a balance control knob 22 after positioning the mode switch 16 in a manual position.

The instrument may also be used for performing automatic sorting operations to discriminate between parts having substantially different characteristics which effect different responses to eddy currents. Again, a manual procedure might be performed for setting up the instrument for a sorting operation but the procedure involved is quite complicated. With the automatic set-up means of the invention, however, it is quite simple. In particular, the mode switch 16 is placed in a sort position and with the probe 12 placed against a sample part of one type, the scan button 18 is depressed and the hold light 20 is energized. After it becomes deenergized, the probe 12 is placed against another sample part of different characteristics and the scan button 18 is again depressed. The hold signal light 20 is again energized for a short time, then becomes deenergized and then it becomes energized for a short time interval, blinking to signal that the instrument is properly set-up for a sorting operation. Then, when the probe is placed against a part of unknown characteristics, the pointer 15 will read either lower or higher than a certain reference indication indicated by a line 23 on the scale of the meter 14. If it reads lower than the reference indication, it means that the part has characterstics like those of the first sample part used in performing the prior set-up operation. If it reads higher, it means that the part has characteristics like those of the second sample part used in the prior set-up operation.

As above noted, the instrument may be used in conventional fashion in a manual mode in which case, the switch 17 may be moved to a low, medium or high position for adjustment of sensitivity.

At any time, the frequency of operation may be determined by turning the control knob 17 to a "FREQ" position, and the position of the meter pointer 15 will then indicate the frequency of operation.

In many cases, it may be desirable to adjust a frequency control knob 24. For example, in the setting up of the instrument to obtain lift-off compensation, the probe 12 may be used with and without a shim to check to make sure that the same meter indication is obtained with and without the shim. If there is any difference, the frequency control 24 may be adjusted until exactly the same reference indication is obtained with and without the shim. It is noted that in either the lift-off mode or the sorting mode, the frequency control knob 24 may effect a frequency adjustment of about ten percent of the full range of the instrument while in the manual mode, adjustment of the knob 24 adjusts the frequency over the full range of the instrument.

The foregoing procedures are readily performed by any operator with minimal instruction and with minimal knowledge of the functioning of the instrument.

Figure 2:
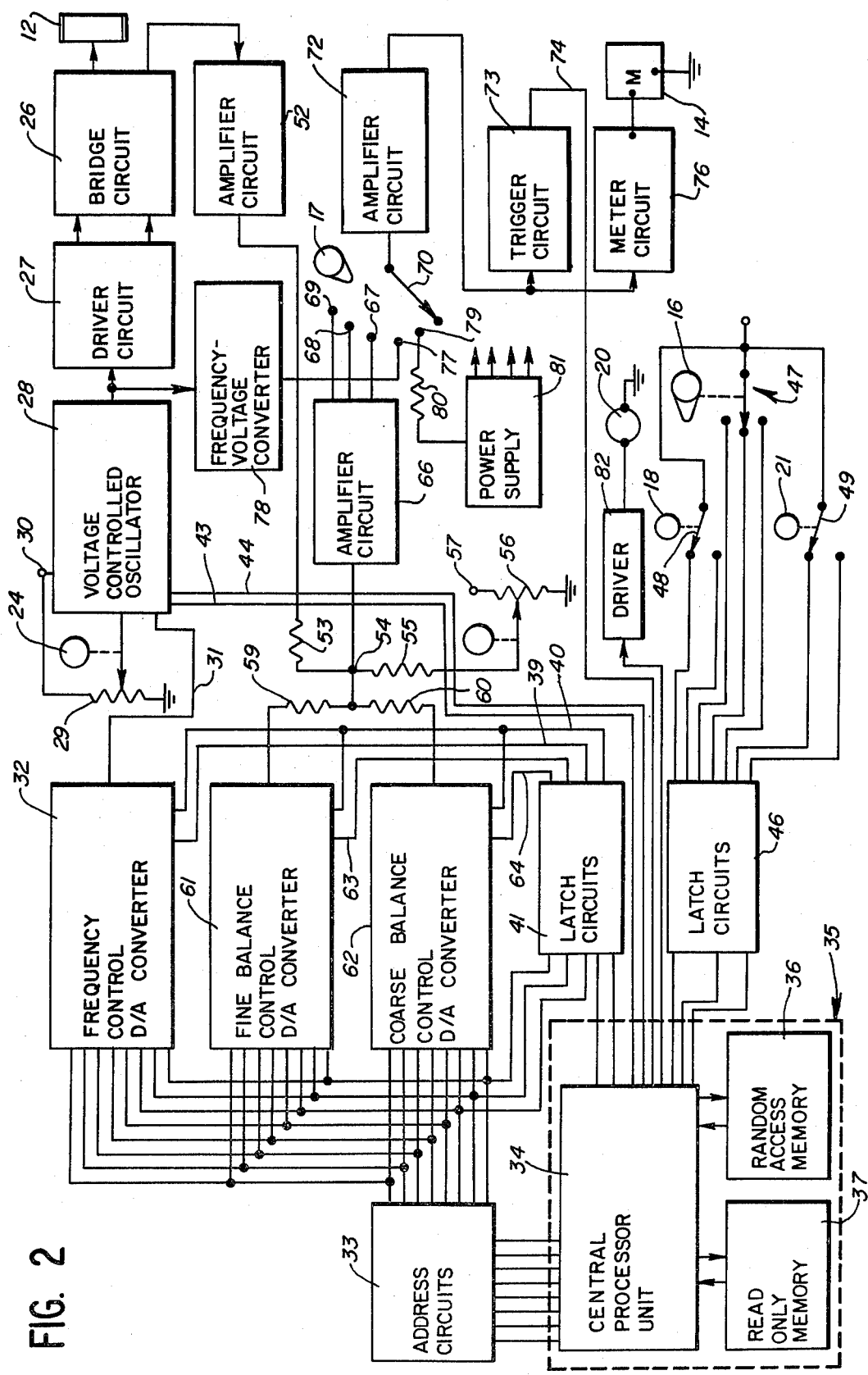
FIG. 2 is a block diagram of circuitry of the instrument of FIG. 1.

FIG. 2 is a block diagram of circuitry of the instrument 10. The probe 12 is connected to a bridge circuit 26 which is driven through a driver circuit 27 from a voltage controlled oscillator circuit 28. The frequency of the voltage controlled oscillator 28 is controllable by an analog signal applied from the movable contact of a potentiometer 29 which is connected between ground and a power supply terminal 30, the position of the contact of the potentiometer 29 being controlled by the knob 24. For the automatic set-up operation, the frequency of the voltage controlled oscillator 28 is controllable by an analog signal applied through line 31 from the output of a digital-to-analog converter 32. The digital-to-analog converter 32 has eight inputs connected through address circuits 33 to a central processor unit 34 of a microcomputer 35 which includes a random access memory 36 and a read only memory 37. The converter 32 also has inputs connected through lines 39 and 40 to latch circuits 41 connected to the central processing unit 34.

For control of the voltage controlled oscillator 28, control inputs thereof are connected through lines 43 and 44 to the central processor unit 34.

The central processor unit 34 is also coupled to switches which are controlled by the mode select knob 16 and the "scan" and "balance" push-butttons 18 and 21. As shown diagrammatically, the central processor unit is connected through what may be designated as scan, balance and interrupt lines to latch circuits 46 which are connected to fixed contacts of a selector switch 47 controlled by the knob 16, a switch 48 controlled by the push-button 18 and a switch 49 controlled by the push-button 21, movable contacts of the switches 47, 48 and 49 being connected to a power supply terminal 50.

In general, the operation is such that when the mode selector switch 47 is in either the lift-off or sort positions and when the switch 48 is operated by the scan button 18, the processor operates through the digital-to-analog circuit 32 to cause the frequency of the voltage controlled oscillator 28 to be changed in increments to a full range of frequencies.

At the same time, output signals from the bridge circuit 26 are effectively recorded in the random access memory 36 of the microcomputer. When two sets of signals have been recorded, the computer circuitry then operates to determine the optimum frequency of operation for the voltage controlled oscillator, then recording the optimum frequency in the random access memory 36, the oscillator 28 being then operated at that frequency.

In the preferred embodiment of the instrument as illustrated, the output signals from the bridge circuit 26 are not directly recorded but are recorded through the operation of circuitry which is also used for an automatic balancing operation as described hereinafter in connection with flow charts of the system. The circuitry includes an amplifier 52 which has an input connected to the bridge circuit and an output connected through a resistor 53 to a circuit point 54 which constitutes a summing point. Circuit point 54 is connected through a resistor 55 to the contact of a potentiometer 56 connected between ground and a power supply terminal 57. The contact of the potentiometer 56 is controlled by the balance control knob 22. In addition, the circuit point 54 is connected through resistors 59 and 60 to outputs of digital-to-analog converters 61 and 62 which have inputs connected to the address circuits 33. Control inputs of both converters 61 and 62 are connected through line 40 to latch circuits 41 and additional control inputs are connected through lines 63 and 64 to the latch circuits 41.

The converter 61 operates as a "fine" control while the converter 62 operates as a "coarse" control, the degree of control being determined by the values of the resistors 59 and 60. By way of example, the resistor 59 may have a value of 1.8 megohms while the resistor 60 may have a resistor of 18 kilohms.

The circuit point 54 is connected to the input of an amplifier circuit 66 which has three outputs connected to contacts 67, 68 and 69 engageable by a selector switch contact 70 coupled to the control knob 17 of the instrument. The contact 70 is connected to the input of an amplifier 72 which has an output connected to the input of a trigger circuit 73 which is connected through a line 74 to the central processor unit 34 and also to the input of a meter circuit 76 which is connected to the meter 14.

In the "FREQ" position of the knob 17, the selector switch contact 70 is engageable with a contact 77 which is connected to the output of a frequency-to-voltage converter circuit 78, circuit 78 having an input connected to the output of the oscillator 28.

In a "TEST" position of the knob 17, the contact 70 is engaged with a contact 79 connected through a resistor 80 to the power supply circuitry 81 which includes a battery, the condition of charge of the battery being indicated by the meter 14 in the test position of the knob 17. The power supply circuitry 81 may be of conventional construction and is not illustrated in detail.

For energization of the "HOLD" signal light 20, it is connected through a driver circuit 82 to an output of the central processor unit 34.

Figure 3:
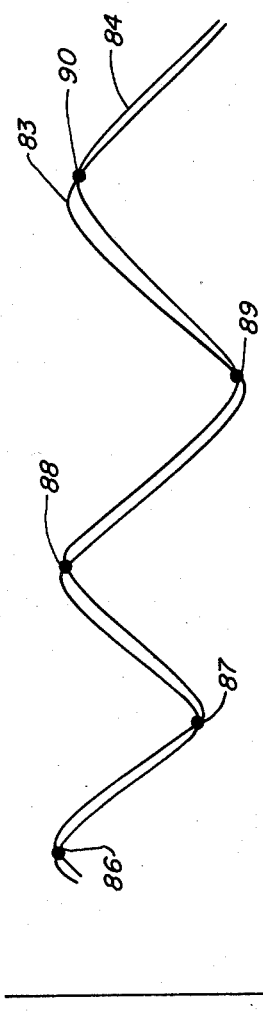
FIG. 3 is a graph illustrating curves recorded during a set-up operation for lift-off compensation.

FIG. 3 graphically illustrates the type of response characteristics obtained with the instrument 10, showing curves 83 and 84 respectively obtained with and without a shim between the end of the probe 12 and the surface of the part 13. The curves 83 and 84 are plots of the output signal of the bridge 26 versus the frequency of operation of the voltage controlled oscillator 28. With the illustrated curves, there are five crossover points 86–90 at which the same responses are obtained with and without the shim and at which the system might be operated to obtain lift-off compensation. The crossover point 90 which is closest to the highest frequency of operation is the preferred point for operation of the system and is automatically selected by the system of the invention.

In the system of the invention, the crossover point 90 is established by first operating with a shim over the entire range of frequencies of the unit, performing a scanning operation and recording in the random access memory 36 a set of signals which define the curve 83. Then, performing a scanning operation without a shim, another set of signals are recorded, thereby defining the curve 84. The microcomputer 35 then operates to determine the point 90. First, starting at the highest frequency and progressively lowering the frequency, the frequency of the first resonant peak is established in a manner as hereinafter described and then the crossover point above that frequency, i.e., the crossover point 90, is established by determining the frequency at which the output signals are equal.

Figure 4:
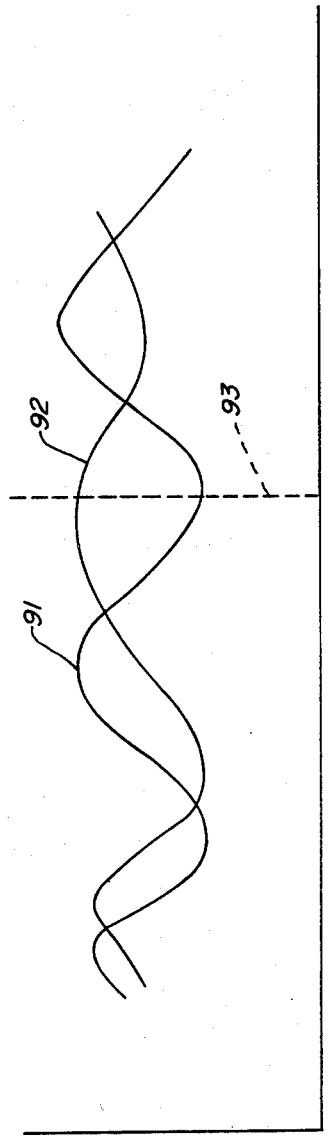
FIG. 4 is a graph illustrating curves recorded during a set-up operation prior to sorting of parts.

FIG. 4 graphically illustrates curves 91 and 92 for explanation of the sorting operation, such curves being plots of the output of the bridge circuit 26 versus the frequency of operation of the oscillator 28. In the example, curve 91 is the curve obtained from the first sample tested, the data used in generating the curve being designated as "DATA 1". Similarly, curve 92 represents the response obtained from the second sample tested, the data being designated as "DATA 2". After recording of the data signals, the microcomputer 35 operates to determine the frequency at which there is a maximum difference between the output signals attained, the frequency being indicated by the vertical line 93 in FIG. 4. The system is then operated at the frequency indicated by line 93 and it provides a maximum degree of discrimination between samples of the type used in connection with the sorting set-up operation.

Before considering the details of the lift-off and sorting set-up operations, it will be helpful to consider the automatic balance operation which is used in recording the data for both the lift-off and sorting set-up operations. The trigger circuit 73 is used in the automatic balance operation and is set to trigger at a certain level which may be adjusted by a suitable control within the circuit. The input of the trigger circuit 73 is connected through the amplifier 72 and the selector switch contact 70 to one of the terminals 67 or 69 connected to the amplifier 66 which has an input connected to the summing point 64. The potential of the summing point 64 is determined by the sum of four signals. The first of the four signals is a signal proportional to the bridge circuit 26, applied to the resistor 53. The second signal is determined by the position of the balance potentiometer 56, applied through the resistor 55. The third signal is determined by the output of the digital-to-analog converter 61, applied through resistor 59 and the fourth signal is determined by the output of the converter 62, applied through the resistor 60.

Figure 5:
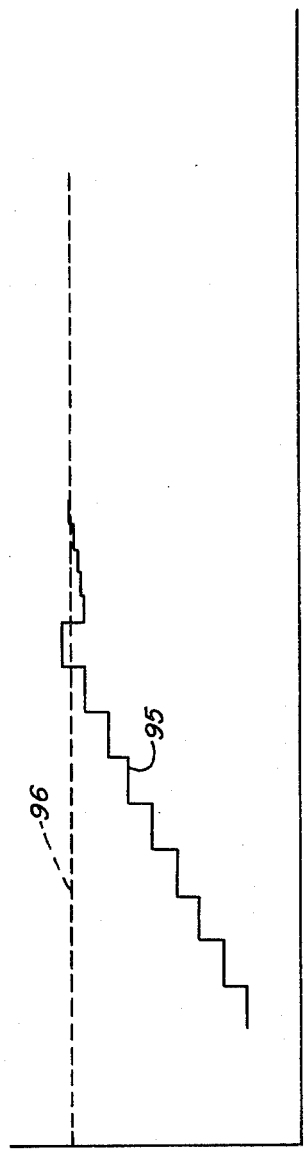
FIG. 5 is a graph illustrating the form of signals produced during a balancing operation.

Manual balance may be performed by adjustment of the knob 22 to adjust the position of the potentiometer 56 and to obtain a predetermined meter reading, indicated by a suitable mark on the scale of the meter 14. To obtain an automatic balance, the trigger circuit 73 is utilized. The operation may be clarified with reference to FIG. 5 and the flow chart of FIG. 10. FIG. 5 illustrates how the input signal to the trigger circuit 73 varies with time during a typical sequence in the automatic balance operation. In the operation as depicted in FIG. 5, the input signal to the trigger circuit 73, indicated by reference numeral 95, is initially below a trigger level indicated by the horizontal dotted line 96 in FIG. 5. This condition is sensed by the microcomputer 35, through the signal applied through line 74 from the output of the trigger circuit 73 and the microcomputer then operates through the "coarse" digital-to-analog converter 62 to increment the output of the converter 62 in steps, thereby increasing the input signal to the trigger circuit 73 as indicated by line 95. When the input signal to the trigger circuit 73 is incremented to a level above the trigger level, the condition is sensed by the computer 35 from the output signal applied through line 74 and the microcomputer then operates through the converter circuit 62 to decrement the level until the input to the trigger circuit 73 is below the trigger level. Then the "fine" converter 61 is brought into operation, incrementing the level of the signal in small increments until the input level is above the trigger level.

If when the balancing operation is initiated, the input level is higher than the trigger level, the "coarse" converter 62 is not initially incremented but is decremented until the level is below the trigger level, then "fine" converter 61 being then incremented until the level is above the trigger level.

Thus, in either case, whether the input level is below or above the trigger level, the final step is a "fine" increment to a level just above the trigger level. Once established, the level is maintained until another balance operation is performed.

The balancing operation is performed in response to operation of the balance push-button 21 and a similar operation is also used for measuring and recording of data in the scan operations performed in response to operation of the scan button 18 to obtain the lift-off and sorting set-up operations. In such scan operations, the frequency control converter 32 is stepped to change the frequency of operation of the oscillator 28 in steps from one end of its range to the other and preferably back to the starting end. Scanning in both directions is desirable in most applications to minimize the effect of delays between changes in frequency and the development of the corresponding output signals.

Initially and after each increment of frequency change, the balancing arrangement is used to shift the level of the output of the "coarse" converter 62 in one direction or the other until a balance is obtained. The digital data supplied to the converter 62 to obtain the balance is then recorded as an indication of the level of the output signal of the bridge circuit 26. It is noted that it is generally unnecessary and undesirable to use the "fine" converter for measurement and recording of the output signal level because of limitations on the accuracy of available converters.

The use of the balancing circuit during scanning has important advantages including the reduction in the circuitry required and the fact that there is generally only a relatively small change in output level when the frequency is stepped and hence the number of incremental or decremental changes required in the operation of the converter 62 is minimized so that the time required for the scan operation is also minimized.

Figure 6:
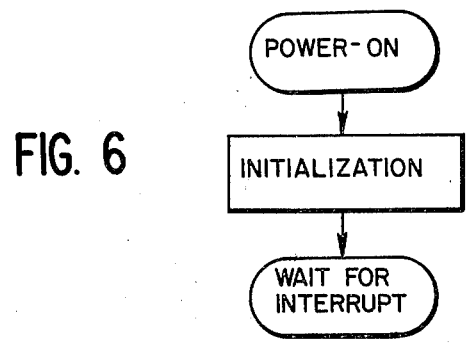
FIGS. 6, 7, 8, 9 and 10 are flow charts illustrating the operation of the instrument
Figure 7:
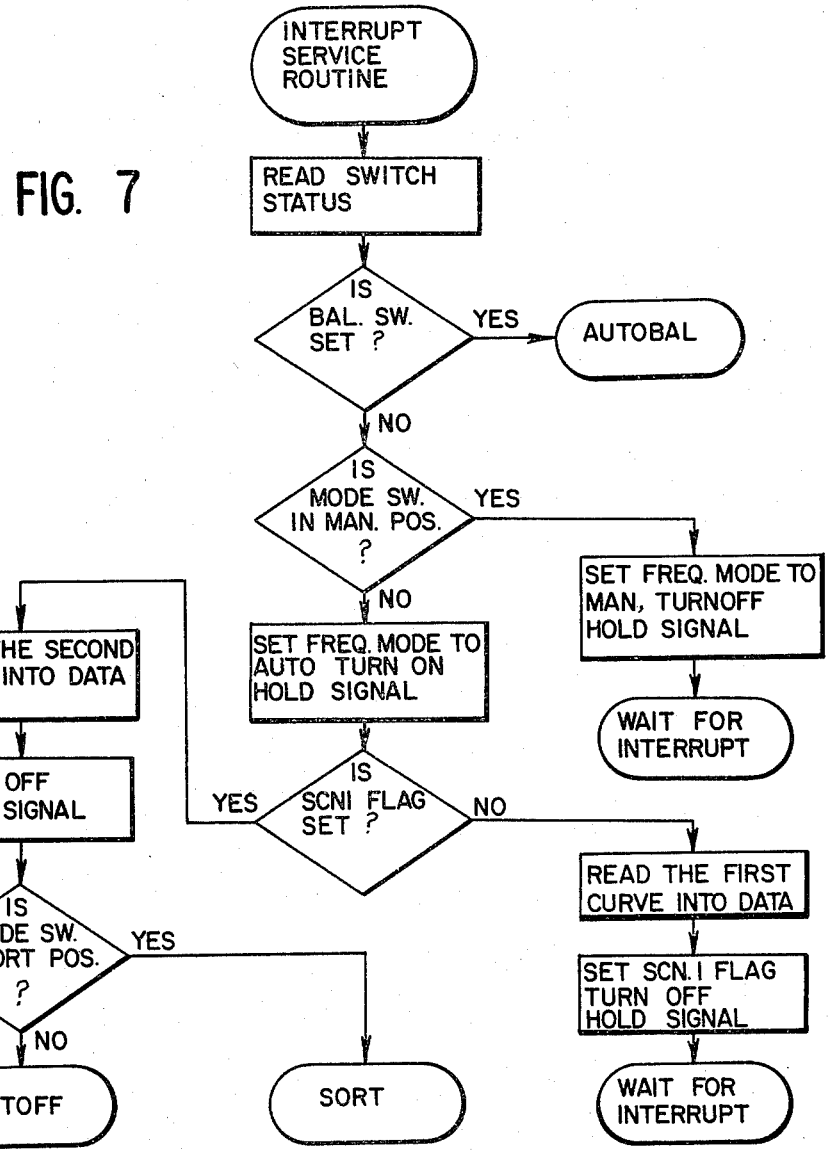
Figure 8:
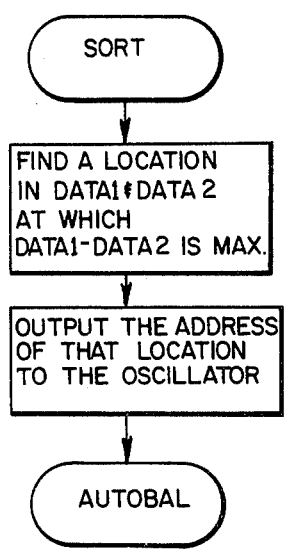
Figure 9:
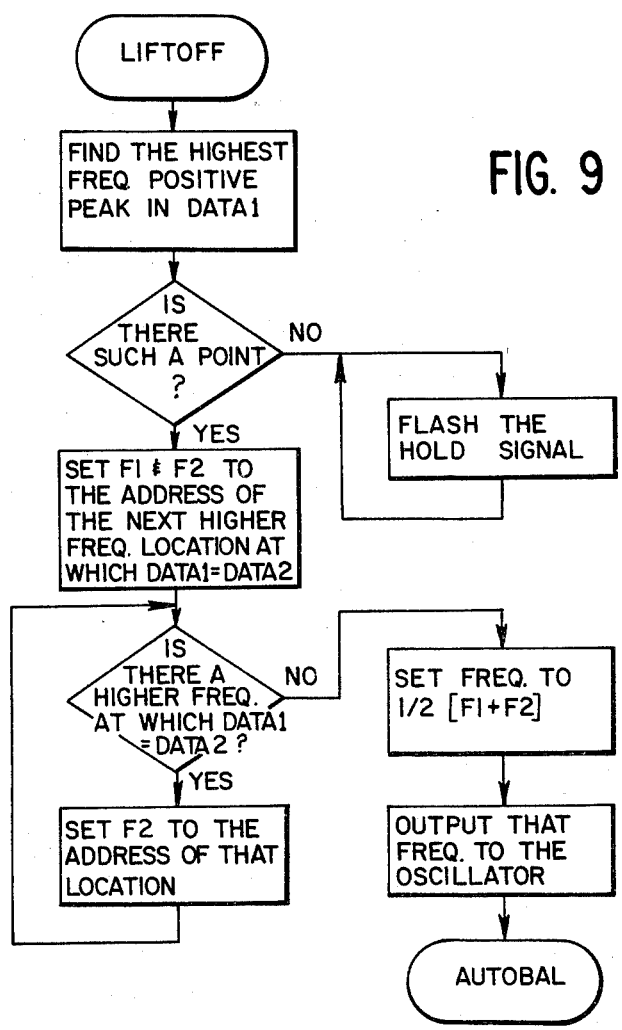
Figure 10:
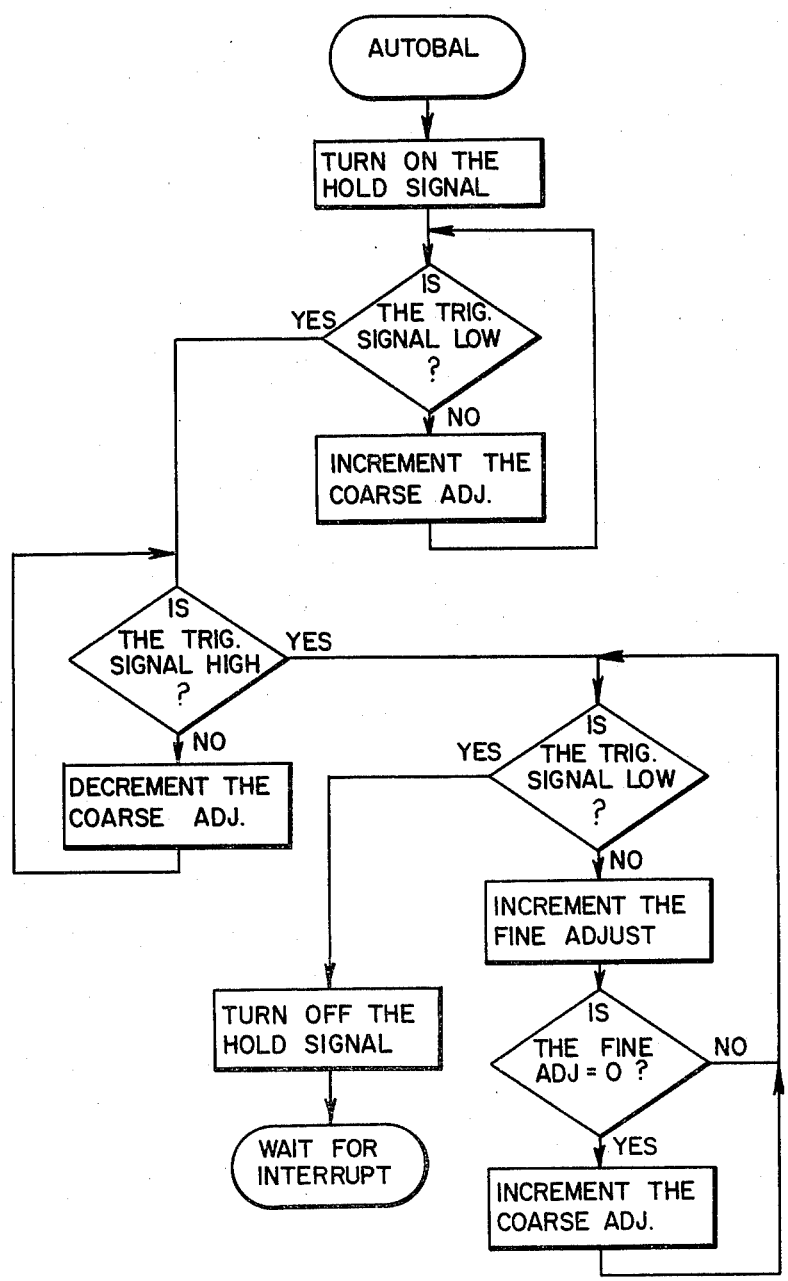

FIGS. 6, 7, 8, 9 and 10 are flow charts illustrating the operation of the system. As indicated in FIG. 6, the system is energized after power is applied and then waits for an interrupt which is produced when either the scan push-button 18 or the balance push-button 21 is depressed. As indicated in FIG. 7, when an interrupt is produced, the switch status is determined and if the balance switch 49, operated by push-button 21, is then set, an automatic balance operation is performed as shown in FIG. 10 and as described hereinbefore. If the balance switch is not then set, and if the mode switch 47 which is operated by knob 16 is not in the manual position, the frequency mode is set to automatic and the hold signal is turned on in response to the set condition of the switch 48 operated by the scan button 18. The frequency mode is set to automatic through signals applied through lines 43 and 44 to the oscillator 28 and through signals applied through lines 39 and 40 to the frequency control digital-to-analog converter 32. The hold signal effects energization of the hold signal light 20 through the drive circuit 80.

Then a determination is made as to whether a "SCAN 1" flag is set. If not, a first curve is read into a "DATA 1" portion of the random access memory 36, this being accomplished by incrementing the frequency in the manner as described hereinbefore, and recording the corresponding digital signals applied to the "fine" and "coarse" converters 61 and 62 to obtain a balance. After reading the first curve, the "SCAN 1" flag is set, the hold signal is turned off and the system waits for an interrupt. Then if there has been no change in the status of the balance and mode switches 49 and 47 and if the scan switch 48 is operated by the scan button at a subsequent interrupt, a second curve is read into a "DATA 2" portion of the random access memory 36 after which the hold signal is turned off to deenergize the light 20. Then a determination is made as to whether the mode switch is in the sort position or the lift position and an operation is performed as shown in either FIG. 8 or FIG. 9.

In the sort operation as depicted in FIG. 8, a location is found at which the difference between the data recorded in the "DATA 1" and "DATA 2" portions of the memory 36 is at a maximum, the address of that location being then output to the control converter 32 for the oscillator 28 which is then operated at that frequency after which an automatic balance operation is performed.

In the lift-off operation as depicted in FIG. 9, the highest frequency positive peak in the "DATA 1" portion of the memory is determined. Such a determination is preferably accomplished by starting at the high end of the frequency range and scanning in a downward direction, while comparing the data at a pair of frequency points spaced a certain number of steps apart, for example, twenty steps, and an intermediate point halfway therebetween. If the output data for the pair of spaced points are equal and the output data for the intermediate point is a predetermined number of increments higher than that for the pair of points (eight increments for example), it indicates the existence of a positive peak at about the intermediate point. This arrangement helps to insure against indicating false peaks due to random noise signals and fluctuations.

After determining the existence and location of the highest frequency positive peak in the "DATA 1" portion of memory, a determination is made as to the location of the first crossover point at any frequency thereabove. This is preferably accomplished by incrementing the frequency, determining the first higher frequency at which the data in the "DATA 1" and "DATA 2" portions are equal, then proceeding with the frequency incrementing and determining the highest frequency thereabove at which such data are equal, and then establishing the average of such frequencies by adding the two frequencies and dividing by two. This specific procedure provides a very accurate location of the crossover point, it being noted that in the vicinity of the crossover point, the two data are very close together and they may be equal at a number of locations, especially when there are noise signals and the like. By determining and averaging the highest and lowest frequencies at which the two data are equal, an accurate measurement is obtained.

Figure 11:
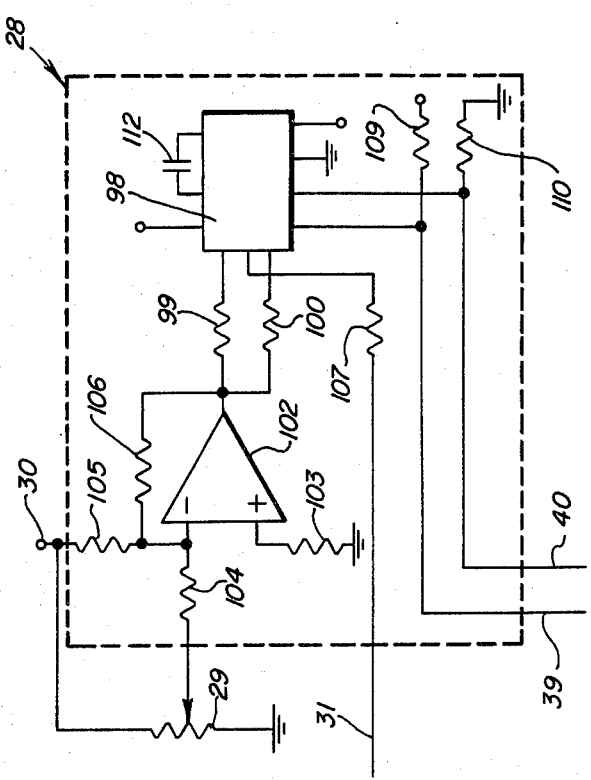
FIG. 11 shows circuitry of a voltage-controlled oscillator of the instrument.

FIG. 11 shows the circuitry of the voltage controlled oscillator 28. An integrated circuit 98 which may be a type 2207 circuit, for example, has terminals connected through resistors 99 and 100 to the output of an operational amplifier 102 which may be a type TL0801. A plus input of the amplifier 102 is connected through a resistor 103 to ground and a minus input thereof is connected through a resistor 104 to the contact of potentiometer 29, through a resistor 105 to the power supply terminal 30 and through a resistor 106 to its output. Another terminal of circuit 98 is connected through a resistor 107 and line 31 to the output of the converter 32. Central terminals are connected to lines 39 and 40 which are respectively connected through resistors 109 and 110 to power supply terminal 30 and ground.

The frequency range of operation of the circuit 98 is controlled in part by the value of a capacitor 112 connected between terminals thereof and may be from about 55 KHz to 200 KHz. In the manual mode of operation, the control signals applied through lines 39 and 40 are such that the frequency is adjustable over the full range by adjustment of potentiometer 29. In the lift-off and sort modes, the frequency incremented during the scan operation from a value close to the low end of the range to a frequency close to the high end of the range through incrementing of the analog signal applied through line 31 from the digital-to-analog converter 32. By way of example, there may be on the order of 255 increments in frequency. The potentiometer 29 is effective in the lift-off mode but the range of possible adjustment is only a small fraction of the full range, on the order of 10% by way of example.

Figure 12:
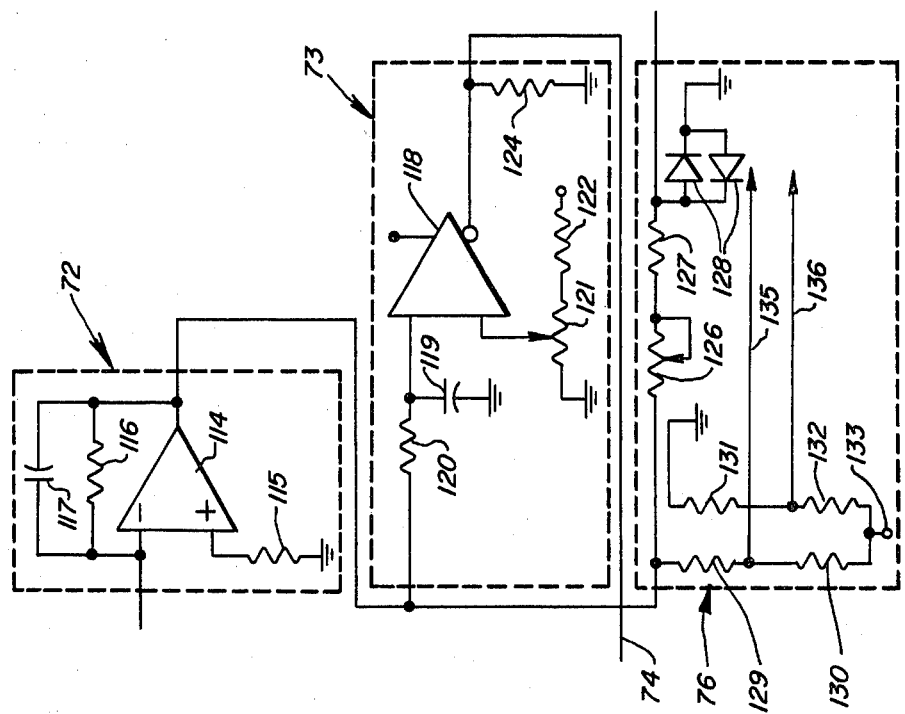
FIG. 12 shows circuitry of an amplifier, a trigger circuit and a meter circuit of the instrument.

FIG. 12 shows the circuitry of the amplifier 72, trigger circuit 73 and meter circuit 76. The amplifier 72 includes an operational amplifier 114 having a plus input connected through a resistor 115 to ground and a minus input connected to switch contact 70 and also through a resistor 116 and a parallel capacitor 117 to its output. The trigger circuit 73 includes an integrated circuit 118 having one input connected through a capacitor 119 to ground and through a resistor 120 to the output of amplifier 72. A second input is connected to the contact of a threshold level adjustment potentiometer 121 which has one terminal connected to ground and its other end terminal connected through a resistor 122 to a power supply terminal 123. The output of circuit 118 is connected to line 74 and through a resistor 124 to ground.

The meter circuit 76 includes an adjustable resistor 126 for control of sensitivity, connected in series with a fixed resistor 127 to the meter 14, a pair of oppositely poled protective diodes 128 being connected across meter 14. Resistors 129-132 form a pair of divider circuits connected between a power supply terminal 133 and and the output of amplifier 72 and ground, respectively, for developing output level and reference level signals on lines 135 and 136 which are usable for control and signalling purposes.

By way of example and not by way of limitation, the components of the illustrated circuits may have values or may be of types as follows:

| Reference Numeral | Value or Type |
| --- | --- |
| 32 | AD7524 |
| 53 | 10,000 ohms |
| 55 | 330,000 ohms |
| 59 | 1.8 megohms |
| 60 | 18,000 ohms |
| 61 | AD7524 |
| 62 | AD7524 |
| 98 | 2207 |
| 99 | 3,000 ohms |
| 100 | 30,000 ohms |
| 102 | TL081 |
| 103 | 68,000 ohms |
| 104 | 220,000 ohms |
| 105 | 1 megohm |
| 106 | 100,000 ohms |
| 107 | 2,400 ohms |
| 109 | 10,000 ohms |
| 110 | 10,000 ohms |
| 112 | 390 picofarads |
| 114 | TL081 |
| 115 | 68,000 ohms |
| 116 | 300,000 ohms |
| 117 | 1500 picofarads |
| 118 | LM311 |
| 119 | 0.001 microfarads |
| 120 | 6,800 ohms |
| 121 | 5,000 ohms |
| 122 | 13,000 ohms |
| 124 | 10,000 ohms |
| 126 | 5,000 ohms |
| 127 | 7,500 ohms |
| 128 | IN4001 |
| 129 | 68,000 ohms |
| 130 | 5,100 ohms |
| 131 | 68,000 ohms |
| 132 | 5,100 ohms |

The probe 12, bridge circuit 26 and driver circuit 27 may be similar to probes and circuits of a Type ED-520 conductivity measuring instrument manufactured and sold by Magnaflux Corporation of Chicago, Ill., of a type as disclosed in U.S. Pat. No. 2,939,073.

The microcomputer 35 may be a Type 1802 computer manufactured by RCA. A program table for effecting the operations depicted in the flow charts of FIGS. 6–10 and described hereinbefore is as follows:

PROGRAM TABLE

```
00003                              LIST     TRM
00004                              SECTION  ED520
00005      0800                    ORG      800H
00006                          ;
00007      0300         DATA2     EQU      0300H       ;STORAGE FOR SCAN2
00008                          ;
00009      0200         DATA1     EQU      0200H       ;STORAGE FOR SCAN1
00010                          ;
00011      8C00         FREE      EQU      8C00H       ;FREE RAM AREA (2 BYTES)
00012                          ;
00013  0800 7B          MAIN      SEQ                  ;LITE LED
00014  0801 F809                  LDI      HI(ISR)     ;SET-UP INT.
00015  0803 B1                    PHI      R1
00016  0804 F8A7                  LDI      LO(ISR)
00017  0806 A1                    PLO      R1
00018  0807 F800                  LDI      0           ;CLEAR UPPER HALF OF
00019  0809 B7                    PHI      R7          ;7,
00020  080A B8                    PHI      R8          ;8,AND
00021  080B BC                    PHI      RC          ;C.
00022  080C F87F                  LDI      7FH         ;INITIALIZE
00023  080E AC                    PLO      RC          ;COARSE&FINE
00024  080F A8                    PLO      R8          ;COUNTERS
00025  0810 EC                    SEX      RC
00026  0811 61                    OUT      1
00027  0812 E8                    SEX      R8
00028  0813 67                    OUT      7
00029  0814 F881                  LDI      81H         ;SET-UP FREQ&GAIN MODE
00030  0816 B9                    PHI      R9
00031  0817 F880                  LDI      80H         ;SET-UP SWITCH REG.
00032  0819 A9                    PLO      R9
00033  081A E3                    SEX      R3          ;SET FREQ. MODE
00034  081B 65                    OUT      5           ;TO MANUAL
00035  081C 81                    BYTE     81H
00036  081D 7A          MORED     REQ                  ;SHUT-OFF LED
00037  081E 3D21                  BN2      DISP        ;DISPLAY OPTION?
00038  0820 00                    IDL                  ;NO,WAIT HERE
00039                                                  ;FOR INTERRUPT
00040  0821 89          DISP      GLO      R9          ;DISPLAY STATUS
00041  0822 AB                    PLO      RB
00042  0823 99                    GHI      R9
00043  0824 BB                    PHI      RB
00044  0825 8C                    GLO      RC
00045  0826 AA                    PLO      RA
00046  0827 87                    GLO      R7
00047  0828 BA                    PHI      RA
00048  0829 E3                    SEX      R3          ;DISABLE
00049  082A 71                    DIS                  ;INTERRUPTS
00050  082B 33                    BYTE     33H
00051  082C D4                    SEP      R4          ;DISPLAY STATUS
00052  082D 81A6                  WORD     81A6H
00053  082F E3                    SEX      R3          ;ENABLE
00054  0830 70                    RET                  ;INTERRUPTS
00055  0831 33                    BYTE     33H
00056  0832 301D                  BR       MORED
00057  0834 89          LOOK      GLO      R9          ;GET SW. STATUS
00058  0835 FA40                  ANI      40H         ;FALSE ?
00059  0837 CA097A                LBNZ     AUTBAL      ;DO AUTO-BAL.
00060  083A 89                    GLO      R9          ;L.O. OR SORT?
00061  083B FA03                  ANI      03H
00062  083D 3A48                  BNZ      SCNCHK      ;YES,CHECK SCANSW.
00063  083F 99          MANUAL    GHI      R9          ;RESET FLAGS
00064  0840 FA81                  ANI      81H
00065  0842 B9                    PHI      R9
00066  0843 E3                    SEX      R3          ;SET FREQ.&GAIN
```

```
00067 0844 65              OUT     5           ;TO MANUAL
00068 0845 01              BYTE    01H
00069 0846 301D  >         BR      MODED       ;AND DISPLAY STATUS
00070 0848 E3        SCNCHK SEX    R3          ;SET FREQ. MODE
00071 0849 65              OUT     5           ;TO AUTOMATIC
00072 084A 02              BYTE    02H
00073 084B 99              GHI     R9
00074 084C FAFE            ANI     0FEH
00075 084E F902            ORI     02H
00076 0850 B9              PHI     R9
00077 0851 FA08            ANI     08H         ;SCN1 FLAG SET?
00078 0853 3A82  >         BNZ     SCAN2       ;IF 1ST SCN,DO 2ND.
00079                  ;
00080 0855 7B        SCAN1 SEQ                 ;LITE LED
00081 0856 F802            LDI     HI(DATA1)   ;POINT TO
00082 0858 BE              PHI     RE          ;DATA1
00083 0859 F800            LDI     LO(DATA1)
00084 085B AE              PLO     RE
00085 085C EE        SCAN10 SEX    RE          ;OUT FREQ. TO
00086 085D 62              OUT     2           ;D-A
00087 085E 2E              DEC     RE          ;ADJUST X
00088 085F D4              SEP     R4          ;CALL A-D
00089 0860 09D4  >         WORD    ATOD        ;SUBROUTINE
00090 0862 8C              GLO     RC          ;GET LEVEL
00091 0863 5E              STR     RE          ;STORE IN DATA1
00092 0864 1E              INC     RE          ;POINT TO NEXT
00093 0865 8E              GLO     RE          ;DATA1 FULL?
00094 0866 3A5C  >         BNZ     SCAN10      ;NO GET MORE
00095 0868 2E        SCAN11 DEC    RE          ;RE-ADJUST X
00096 0869 EE              SEX     RE
00097 086A 62              OUT     2           ;OUTPUT FREQ.
00098 086B 2E              DEC     RE          ;ADJUST X
00099 086C D4              SEP     R4          ;CALL A-D ROUTINE
00100 086D 09D4  >         WORD    ATOD
00101 086F 8C              GLO     RC          ;GET LEVEL
00102 0870 EE              SEX     RE
00103 0871 F4              ADD                 ;AVERAGE OLD&NEW
00104 0872 76              SHRC                ;DATA LEVELS
00105 0873 5E              STR     RE          ;AND STORE AT <X>
00106 0874 8E              GLO     RE          ;FINISHED?
00107 0875 3A68  >         BNZ     SCAN11      ;NO,CONTINUE
00108 0877 7A              REQ                 ;SHUT OFF LED
00109 0878 89              GLO     R9          ;RESET SCN SW.
00110 0879 FAEF            ANI     0EFH       ;FLAG BIT
00111 087B A9              PLO     R9          ;
00112 087C 99              GHI     R9          ;SET SCN1
00113 087D F908            ORI     08H         ;FLAG BIT
00114 087F B9              PHI     R9
00115 0880 301D  >         BR      MODED
00116                  ;
00117 0882 7B        SCAN2 SEQ                 ;LITE LED
00118 0883 F803            LDI     HI(DATA2)   ;POINT TO
00119 0885 BE              PHI     RE          ;DATA2
00120 0886 F800            LDI     LO(DATA2)
00121 0888 AE              PLO     RE
00122 0889 EE        SCAN20 SEX    RE          ;OUT FREQ TO
00123 088A 62              OUT     2           ;D-A
00124 088B 2E              DEC     RE          ;ADJUST X
00125 088C D4              SEP     R4          ;CALL A-D
00126 088D 09D4  >         WORD    ATOD        ;SUBROUTINE
00127 088F 8C              GLO     RC          ;GET LEVEL
00128 0890 5E              STR     RE          ;PUT IN DATA2
00129 0891 1E              INC     RE
00130 0892 8E              GLO     RE          ;DATA2 FULL?
00131 0893 3A89  >         BNZ     SCAN20
```

```
00132 0895 2E          SCAN21  DEC     RE              ;READJUST X
00133 0896 EE                  SEX     RE
00134 0897 62                  OUT     2               ;OUTPUT FREQ.
00135 0898 2E                  DEC     RE              ;ADJUST X
00136 0899 D4                  SEP     R4              ;CALL A-D ROUTINE
00137 089A 09D4       >        WORD    ATOD
00138 089C 8C                  GLO     RC              ;GET LEVEL
00139 089D EE                  SEX     RE
00140 089E F4                  ADD                     ;AVERAGE OLD&NEW
00141 089F 76                  SHRC                    ;DATA LEVELS
00142 08A0 5E                  STR     RE              ;AND STORE AT X
00143 08A1 8E                  GLO     RE              ;FINISHED?
00144 08A2 3A95      >         BNZ     SCAN21          ;NO,CONTINUE
00145 08A4 7A                  REQ                     ;SHUT OFF LED
00146 08A5 89                  GLO     R9              ;RESET SCN SW.
00147 08A6 FAEF                ANI     0EFH            ;FLAG BIT
00148 08A8 A9                  PLO     R9

00149 08A9 89          ENDSCN  GLO     R9              ;LO OR SORT
00150 08AA FA02                ANI     02H
00151 08AC 3ADB      >         BNZ     LOFF            ;DO LIFT-OFF
00152                          ;
00153 08AE F802        SORT    LDI     HI(DATA1)       ;INITILIZE
00154 08B0 BD                  PHI     RD              ;DATA POINTERS
00155 08B1 F803                LDI     HI(DATA2)
00156 08B3 BE                  PHI     RE
00157 08B4 F801                LDI     LO(DATA1+1)
00158 08B6 AD                  PLO     RD
00159 08B7 AE                  PLO     RE
00160 08B8 F88C                LDI     8CH             ;POINT TO RAM
00161 08BA BF                  PHI     RF
00162 08BB F801                LDI     01H
00163 08BD AF                  PLO     RF
00164 08BE F800                LDI     00H             ;CLEAR DEV0
00165 08C0 5F                  STR     RF
00166 08C1 EE          L2      SEX     RE              ;FIND 1-2
00167 08C2 4D                  LDA     RD
00168 08C3 F7                  SM
00169 08C4 60                  IRX                     ;AND POINT TO NEXT
00170 08C5 3BD2      >         BM      L1              ;NO GOOD,SKIP
00171 08C7 EF                  SEX     RF              ;BIGGER DIFFERENCE?
00172 08C8 F7                  SM
00173 08C9 3BD2      >         BM      L1              ;NO,SKIP
00174 08CB F4                  ADD                     ;YES,PUT IN DEV0
00175 08CC 73                  STXD
00176 08CD 8E                  GLO     RE              ;ADJUST RE.0 AND
00177 08CE FF02                SMI     02H             ;PUT IN F0
00178 08D0 5F                  STR     RF
00179 08D1 60                  IRX
00180 08D2 8E          L1      GLO     RE              ;DONE ??
00181 08D3 3AC1      >         BNZ     L2
00182 08D5 2F                  DEC     RF
00183 08D6 0F                  LDN     RF
00184 08D7 A7                  PLO     R7              ;PUT F0 IN FREQ
00185 08D8 C00949    >         LBR     FREQ
00186                          ;
00187                          ;
00188 08DB F802        LOFF    LDI     HI(DATA1)       ;POINT TO DATA
00189 08DD BF                  PHI     RF
00190 08DE BE                  PHI     RE
00191 08DF BD                  PHI     RD
00192 08E0 F8FF                LDI     0FFH            ;SPREAD POINTERS
00193 08E2 AF                  PLO     RF
00194 08E3 F8DF                LDI     0DFH
00195 08E5 AE                  PLO     RE
```

```
00196 08E6 F8BF           LDI     0BFH
00197 08E8 AD             PLO     RD
00198 08E9 EF       PK0   SEX     RF        ;LOOK FOR PEAK
00199 08EA 0E             LDN     RE
00200 08EB F5             SD
00201 08EC CB0940 >       LBNF    MOREPK
00202 08EF FF08           SMI     08H
00203 08F1 CB0940 >       LBNF    MOREPK
00204 08F4 ED             SEX     RD
00205 08F5 0E             LDN     RE
00206 08F6 F5             SD
00207 08F7 CB0940 >       LBNF    MOREPK
00208 08FA FF08           SMI     08H
00209 08FC CB0940 >       LBNF    MOREPK
00210 08FF F88C    CROSCK LDI     HI(FREE)  ;POINT F TO FREE
00211 0901 BF             PHI     RF
00212 0902 F800           LDI     LO(FREE)
00213 0904 AF             PLO     RF
00214 0905 F800           LDI     0         ;CLEAR FREE
00215 0907 5F             STR     RF
00216 0908 1F             INC     RF
00217 0909 8E             GLO     RE        ;PUT PK IN FREE+1
00218 090A 5F             STR     RF
00219 090B 2F             DEC     RF
00220 090C 8E             GLO     RE        ;POINT D TO E+100H
00221 090D AD             PLO     RD
00222 090E 9E             GHI     RE
00223 090F FC01           ADI     1
00224 0911 BD             PHI     RD
00225 0912 EE       CK0   SEX     RE        ;CALCULATE
00226 0913 0D             LDN     RD        ;DATA1-DATA2
00227 0914 F7             SM
00228 0915 3A30 >         BNZ     CK1       ;NOT =,DO MORE
00229 0917 8F             GLO     RF        ;IS THIS 1ST EQUAL
00230 0918 3A1D >         BNZ     CK2       ;NO,GO AROUND
00231 091A 8E             GLO     RE        ;YES,STORE E.0
00232 091B 5F             STR     RF        ;IN FREE,AND
00233 091C 1F             INC     RF        ;POINT TO FREE+1
00234 091D 8E       CK2   GLO     RE        ;STORE E.0 IN
00235 091E 5F             STR     RF        ;FREE+1
00236 091F 1D       CK3   INC     RD        ;POINT TO NEXT
00237 0920 1E             INC     RE        ;DATA PAIR
00238 0921 8E             GLO     RE        ;HAVE ALL POINTS BEEN
00239 0922 3A12 >         BNZ     CK0       ;NO,DO MORE
00240 0924 8F       CK4   GLO     RF        ;ARE THERE ANY
00241 0925 C20100         LBZ     0100H     ;CROSSPOINTS?,IF
00242                                       ;NOT, GO TO RAM
00243 0928 EF             SEX     RF        ;CALCULATE FREQ
00244 0929 0F             LDN     RF        ;FREQ=(FREE)+(FREE+1)    2
00245 092A 2F             DEC     RF
00246 092B F4             ADD
00247 092C 76             SHRC
00248 092D A7             PLO     R7
00249 092E 3049 >         BR      FREQ
00250                     ;
00251 0930 8F       CK1   GLO     RF        ;HAS A CROSS BEEN?
00252 0931 321F >         BZ      CK3       ;NO,CONTINUE
00253 0933 EE             SEX     RE        ;D=DATA1-DATA2+1
00254 0934 0D             LDN     RD
00255 0935 F7             SM
00256 0936 FC01           ADI     1
00257 0938 321F >         BZ      CK3       ;D=0,CONTINUE
00258 093A FF02           SMI     2
00259 093C 321F >         BZ      CK3
```

```
00260 093E 3024  >         BR     CK4       ;FIND FREQ
00261                  ;
00262                  ;
00315                  ;
00316 097A 7B          AUTBAL SEQ            ;LITE LED
00317 097B 3484  >            B1     DOWN   ;UP OR DOWN?
00318 097D EC          UP     SEX    RC      ;OUTPUT COARSE,
00319 097E 61                 OUT    1       ;AND INCREMENT
00320 097F D4                 SEP    R4      ;WAIT
00321 0980 09EA  >            WORD   DELTA
00322 0982 3C7D  >            BN1    UP      ;REPEAT IF NEC.
00323 0984 EC          DOWN   SEX    RC      ;OUTPUT COARSE,
00324 0985 61                 OUT    1       ;AND DECREMENT
00325 0986 2C                 DEC    RC
00326 0987 2C                 DEC    RC
00327 0988 D4                 SEP    R4      ;WAIT
00328 0989 09EA  >            WORD   DELTA
00329 098B 3484  >            B1     DOWN    ;NOT DONE
00330 098D C4                 NOP
00331 098E C4                 NOP
00332 098F C4                 NOP
00333 0990 E8          FINE   SEX    R8      ;OUTPUT FINE
00334 0991 67                 OUT    7       ;AND INCREMENT
00335 0992 D4                 SEP    R4      ;WAIT
00336 0993 09EA  >            WORD   DELTA
00337 0995 349E  >            B1     EXITB   ;IF PASSED,FINISHED
00338 0997 88                 GLO    R8      ;ELSE IS FINE=0?
00339 0998 3A90  >            BNZ    FINE    ;NO,REPEAT
00340 099A EC                 SEX    RC      ;YES,OUTPUT
00341 099B 61                 OUT    1       ;AND INC. COARSE
00342 099C 3090  >            BR     FINE    ;THEN REPEAT
00343 099E 89          EXITB  GLO    R9      ;RESET BAL.SW.
00344 099F FA6F                ANI    06FH
00345 09A1 A9                 PLO    R9
00346 09A2 7A                 REQ            ;SHUT-OFF LED
00347 09A3 C0061D  >           LBR    MORED  ;GO DISPLAY
00348                  ;
00349                  ;......INTERRUPT SERVICE ROUTINE......
00350                  ;
00351 09A6 70          EXITI  RET
00352 09A7 22          ISR    DEC    R2      ;SAVE <X>
00353 09A8 78                 SAV
00354 09A9 22                 DEC    R2
00355 09AA 73                 STXD
00356 09AB 76                 SHRC
00357 09AC 73                 STXD           ;D&DF
00358 09AD 9F                 GHI    RF
00359 09AE 73                 STXD
00360 09AF 8F                 GLO    RF
00361 09B0 73                 STXD 00362 09B1 F880               LDI    80H     ;WAIT FOR DEBOUNCE
00363 09B3 BF                 PHI    RF
00364 09B4 2F          D1     DEC    RF
00365 09B5 8F                 GLO    RF
00366 09B6 CA09B4  >           LBNZ   D1
00263 0940 8D          MOREPX GLO    RD      ;DONE??
00264 0941 326B  >            BZ     ALARM   ;DO ALARM
00265 0943 2D                 DEC    RD
00266 0944 2E                 DEC    RE
00267 0945 2F                 DEC    RF
00268 0946 C009E9  >           LBR    PK0
00269                  ;
00270                  ;
00271 0949 E7          FREQ   SEX    R7      ;OUTPUT FREQ.
00272 094A 62                 OUT    2
```

```
00273  094B 27               DEC    R7
00274  094C 89               GLO    R9      ;RESET LO,SCN1,
00275  094D FA83              ANI    83H     ;SCN SW. BITS
00276  094F A9               PLO    R9
00277  0950 99               GHI    R9      ;RESET SCN1
00278  0951 FA83              ANI    83H
00279  0953 B9               PHI    R9
00280  0954 E3               SEX    R3
00281  0955 65               OUT    5
00282  0956 02               BYTE   02H
00283  0957 7A        BEEP   REQ            ;BEEP WHEN FINISHED
00284  0958 FFFF              LDI    0FFH
00285  095A BF               PHI    RF
00286  095B 2F        B0     DEC    RF
00287  095C 9F               GHI    RF
00288  095D 3A5B >            BNZ    B0
00289  095F 7B               SEQ
00290  0960 F820              LDI    20H
00291  0962 BF               PHI    RF
00292  0963 2F        BEEP1  DEC    RF
00293  0964 9F               GHI    RF
00294  0965 3A63 >            BNZ    BEEP1
00295  0967 7A               REQ
00296                  ;
00297  0968 C0081D >         LBR    MORED   ;GO TO WAIT MODE
00298                  ;
00299                  ;.....ALARM ROUTINE..........
00300                  ;
00301  096B 7A        ALARM  REQ            ;FLASH LED ON&OFF
00302  096C 3170 >    A0     BU     A1
00303  096E 7B               SEQ
00304  096F 38               SKP
00305  0970 7A        A1     REQ
00306  0971 F820          D9 LDI    20H     ;WAIT AWHILE
00307  0973 BF               PHI    RF
00308  0974 2F        D10    DEC    RF
00309  0975 9F               GHI    RF
00310  0976 3A74 >            BNZ    D10
00311  0978 306C >           BR     A0
00312                  ;
00313                  ;
00314                  ;.....AUTO-BALANCE ROUTINE........
00367                  ;
00368  09B9 F881              LDI    81H     ;POINT <X>
00369  09BB BF               PHI    RF
00370  09BC F800              LDI    0       ;TO "SAFE" AREA
00371  09BE AF               PLO    RF
00372  09BF EF               SEX    RF
00373  09C0 6E               INP    6       ;GET SWITCHES
00374  09C1 A9               PLO    R9
00375  09C2 E2        ASLEEP SEX    R2      ;RESET X
00376  09C3 12               INC    R2
00377  09C4 42               LDA    R2
00378  09C5 BF               PHI    RF      ;RESTORE:
00379  09C6 42               LDA    R2
00380  09C7 AF               PLO    RF      ;RF
00381  09C8 42               LDA    R2
00382  09C9 FE               SHL
00383  09CA 42               LDA    R2      ;DF&D
00384  09CB F908 >            LDI    HI(LOOK)   ;RUN AT LOOK
00385  09CD B3               PHI    R3      ;AFTER INTERRUPTS
00386  09CE F834 >            LDI    LO(LOOK)
00387  09D0 A3               PLO    R3
00388  09D1 C009A6 >         LBR    EXIT1   ;ESCAPE
00389                  ;
00390                  ;
```

```
00391                    ;........A TO D CONVERSION SUBROUTINE.........
00392                    ;
00393                    ;
00394 09D4 34DD  >  ATOD  B1   ADWN     ;UP OR DOWN FIRST?
00395 09D6 EC       AUP   SEX  RC       ;OUTPUT COARSE
00396 09D7 61             OUT  1        ;TO D-A&INC.
00397 09D8 D4             SEP  R4       ;WAIT FOR DATA
00398 09D9 09F1  >        WORD PAUSE    ;TO SETTLE
00399 09DB 3CD6  >        BN1  AUP      ;MORE IF NEC.
00400                    ;
00401 09DD EC       ADWN  SEX  RC       ;OUTPUT COARSE
00402 09DE 61             OUT  1        ;TO D-A&DEC.
00403 09DF 2C             DEC  RC
00404 09E0 2C             DEC  RC
00405 09E1 D4             SEP  R4       ;WAIT FOR DATA
00406 09E2 09F1  >        WORD PAUSE    ;TO SETTLE
00407 09E4 3CE9  >        BN1  EXXIT
00408 09E6 C009DD >       LBR  ADWN
00409 09E9 D5       EXXIT SEP  R5       ;RETURN
00410                    ;
00411                    ;
00412                    ;
00413                    ;........TIME DELAY SUBROUTINE........
00414                    ;
00415 09EA F880      DELTA LDI  80H     ;WASTE TIME
00416 09EC AF              PLO  RF
00417 09ED 2F        D2    DEC  RF
00418 09EE 8F              GLO  RF
00419 09EF 3AED  >         BNZ  D2
00420 09F1 D5        PAUSE SEP  R5      ;RETURN
00421                    ;
00422                           END   SECTION
```

TEKTRONIX    1802 ASM V3.3   SYMBOL TABLE                    PAGE   10

SCALARS

```
    DATA1 -- 0200           DATA2 -- 0300           FREE --- 8C00
    R0 ----- 0000           R1 ----- 0001           R2 ----- 0002
    R3 ----- 0003           R4 ----- 0004           R5 ----- 0005
    R6 ----- 0006           R7 ----- 0007           R8 ----- 0008
    R9 ----- 0009           RA ----- 000A           RB ----- 000B
    RC ----- 000C           RD ----- 000D           RE ----- 000E
    RF ----- 000F
```

ED520 SECTION (09F2)

```
    A0 ----- 096C           A1 ----- 0970           ADWN --- 09DD
    ALARM -- 096B           ASLEEP - 09C2           ATOD --- 09D4
    AUP ---- 09D6           AUTBAL - 097A           B0 ----- 095B
    BEEP --- 0957           BEEP1 -- 0963           CK0 ---- 0912
    CK1 ---- 0930           CK2 ---- 091D           CK3 ---- 091F
    CK4 ---- 0924           CKOSCK - 08FF           D1 ----- 09B4
    D10 ---- 0974           D2 ----- 09ED           D9 ----- 0971
    DELTA -- 09EA           DISP --- 0821           DOWN --- 0984
    ENDSCN - 08A9           EXITB -- 099E           EXITI -- 09A6
    EXXIT -- 09E9           FINE --- 0990           FREQ --- 0949
    ISR ---- 09A7           L1 ----- 08D2           L2 ----- 08C1
    LOFF --- 08DB           LOOK --- 0834           MAIN --- 0800
    MANUAL - 083F           MORED -- 081D           MOREPK - 0940
    PAUSE -- 09F1           PK0 ---- 09E9           SCAN1 -- 0855
    SCAN10 - 085C           SCAN11 - 0868           SCAN2 -- 0882
    SCAN20 - 0889           SCAN21 - 0895           SCNCHK - 0848
    SORT --- 08AE           UP ----- 097D
```

It will be understood that modifications and variations may be effected without departing from the spirit and scope of the novel concepts of this invention.

We claim:

1. In a nondestructive testing system including measuring means for developing an output signal corresponding to characteristics of a structure under test, said measuring means including adjustable means for controlling the value of a test parameter over a certain range, and set-up means for adjusting said adjustable means, said set-up means comprising: memory means for storage of the value of said output signal and the concurrent value of said test parameter, program means for control of said adjustable means and said memory means, said program means being operable under each of a plurality of different set-up test conditions for adjusting the value of said test parameter over said certain range and for simultaneously storing a set of output signal values and concurrent test parameter values, and comparison means associated with said memory means for comparing said sets of stored output signal and test parameter values and for developing and storing an optimum parameter value at which a predetermined correspondence between output signals is obtained during said plurality of different set-up test conditions, and means operative upon storage of said optimum parameter value for then adjusting said adjustable means to obtain said optimum test parameter value during subsequent operation of the said system in testing structures of unknown characteristics.

2. In a nondestructive testing system as defined in claim 1 for developing an output signal which is a function of a first characteristic of a structure under test while being unaffected by a second characteristic of the structure under test, said second characteristic having one value in a first of said set-up test conditions and having a substantially different value in a second of said set-up test conditions, and said comparison means being operable to develop and store an optimum parameter value at which said output signals during said first and second set-up test conditions are equal.

3. In a nondestructive testing system as defined in claim 2 including an eddy current probe arranged to be placed in proximity to a portion of a metal part, one of said first and said second characteristics being the conductivity of said metal parts and the other of said first and second characteristics being the spatial relationship between said probe and said metal part.

4. In a nondestructive testing system as defined in claim 3, said first characteristic being the conductivity of said metal part.

5. In a nondestructive testing system as defined in claim 1 including an eddy current probe and oscillator means for supplying a variable frequency drive signal to said probe, said adjustable means being arranged for controlling the frequency of said oscillator means.

6. In a nondestructive testing system as defined in claim 5, said oscillator means being a voltage-controlled oscillator, and said adjustable means including a digital-to-analog converter for supplying a variable voltage to said oscillator means controlled by digital signals applied thereto.

7. In a nondestructive testing system as defined in claim 6, means for developing digital data corresponding to said output signal values.

8. In a nondestructive testing system as defined in claim 7, microcomputer means for applying digital control signals to said digital-to-analog converter means and including said memory means, said memory means being effective for storing said digital data corresponding to said output signal values, and said microcomputer means further including said comparison means.

9. In a nondestructive testing system as defined in claim 1 for sorting of parts having one or the other of two characteristics, a first of said set-up test conditions being performed with a sample part having one of said characteristics and a second of said set-up test conditions being performed with a part having the other of said characteristics, and said comparison means being operative for storing an optimum parameter value at which a maximum difference is obtained between output signals produced during said first and second set-up test conditions.

10. In a nondestructive testing system as defined in claim 1, balance means operative for producing a predetermined output signal under any selected operating condition.

11. In a nondestructive testing system as defined in claim 10, said balance means being operative during the adjustment of the value of said test parameter over said certain range for determining the value of a balancing signal required to produce a balance at each value of said test parameter, and said program means being operable to store in said memory means the values of said balance signals.

12. In a nondestructive testing system as defined in claim 1, said program means being operable in each of said different set-up test conditions to change the value of said test parameter in progressive steps from one end of said certain range to the other end thereof, said memory means being operable to store digital data corresponding to the value of said output signal at each step of said test parameter, and said comparison means being operable to compare the stored digital data produced during said different set-up test conditions.

13. In a nondestructive testing system as defined in claim 12 for developing an output signal which is a function of a first characteristic of a structure under test while being unaffected by a second characteristic of the structure under test, said set-up test conditions being such that said first characteristic is the same in both first and second set-up test conditions while said second characteristic is substantially different, and said comparison means being operable to develop and store a parameter value at which said stored digital data are substantially equal.

14. In a nondestructive testing system as defined in claim 13, said comparison means being operable to compare said stored data in progressive steps correlated to the progressive steps to change in value of said test parameter and being operable to develop, store and average the first and last parameter values at which said stored digital data are equal.

* * * * *

UNITED STATES PATENT AND TRADEMARK OFFICE
CERTIFICATE OF CORRECTION

PATENT NO. : 4,351,031                        Page 1 of 6

DATED : September 21, 1982

INVENTOR(S) : John J. Flaherty et al.

It is certified that error appears in the above-identified patent and that said Letters Patent is hereby corrected as shown below:

Column 5, line 30, after "charts", "of" should read -- for --.

Column 9, line 33, "TL0801" should read -- TL081 --.

Columns 17 through 26 should be deleted and the attached columns 17 through 26 substituted therefor.

Signed and Sealed this

Twentieth Day of September 1983

[SEAL]

Attest:

GERALD J. MOSSINGHOFF

Attesting Officer    Commissioner of Patents and Trademarks

```
00196 08E6 F86F          LDI    06FH
00197 08E8 AD            PLO    RD
00198 08E9 EF      PK0   SEX    RF       ;LOOK FOR PEAK
00199 08EA 0E            LDN    RE
00200 08EB F5            SD
00201 08EC CB0940  >     LBNF   MOREPK
00202 08EF FF08          SMI    08H
00203 08F1 CB0940  >     LBNF   MOREPK
00204 08F4 ED            SEX    RD
00205 08F5 0E            LDN    RE
00206 08F6 F5            SD
00207 08F7 CB0940  >     LBNF   MOREPK
00208 08FA FF08          SMI    08H
00209 08FC CB0940  >     LBNF   MOREPK
00210 08FF F8C    CROSCK LDI    HI(FREE) ;POINT F TO FREE
00211 0901 BF            PHI    RF
00212 0902 F800          LDI    LO(FREE)
00213 0904 AF            PLO    RF
00214 0905 F800          LDI    0        ;CLEAR FREE
00215 0907 5F            STR    RF
00216 0908 1F            INC    RF
00217 0909 9E            GLO    RE       ;PUT PK IN FREE+1
00218 090A 5F            STR    RF
00219 090B 2F            DEC    RF
00220 090C 9E            GLO    RE       ;POINT D TO E+100H
00221 090D AD            PLO    RD
00222 090E 9E            GHI    RE
00223 090F FC01          ADI    1
00224 0911 BD            PHI    RD
00225 0912 EE      CK0   SEX    RE       ;CALCULATE
00226 0913 0D            LDN    RD       ;DATA1-DATA2
00227 0914 F7            SM
00228 0915 3A30    >     BNZ    CK1      ;NOT =,DO MORE
00229 0917 8F            GLO    RF       ;IS THIS 1ST EQUAL
00230 091A 3A1D    >     BNZ    CK2      ;NO,GO AROUND
00231 091A 9E            GLO    RE       ;YES,STORE E.0
00232 091B 5F            STR    RF       ;IN FREE,AND
00233 091C 1F            INC    RF       ;POINT TO FREE+1
00234 091D 9E      CK2   GLO    RE       ;STORE E.0 IN
00235 091E 5F            STR    RF       ;FREE+1
00236 091F 1D      CK3   INC    RD       ;POINT TO NEXT
00237 0920 1E            INC    RE       ;DATA PAIR
00238 0921 9E            GLO    RE       ;HAVE ALL POINTS BEEN
00239 0922 3A12    >     BNZ    CK0      ;NO,DO MORE
00240 0924 8F      CK4   GLO    RF       ;ARE THERE ANY
00241 0925 C20100        LE=    0100H    ;CROSSPOINTS?,IF
00242                                    ;NOT, GO TO RAM
00243 0928 EF            SEX    RF       ;CALCULATE FREQ
00244 0929 0F            LDN    RF       ;FREQ=(FREE)+(FREE+1)    2
00245 092A 2F            DEC    RF
00246 092B F4            ADD
00247 092C 76            SHRC
00248 092D A7            PLO    R7
00249 092E 3049    >     BR     FREQ
00250                    ;
00251 0930 8F      CK1   GLO    RF       ;HAS A CROSS BEEN?
00252 0931 321F    >     BZ     CK3      ;NO,CONTINUE
00253 0933 EE            SEX    RE       ;D=DATA1-DATA2+1
00254 0934 0D            LDN    RD
00255 0935 F7            SM
00256 0936 FC01          ADI    1
00257 0938 321F    >     BZ     CK3      ;D=0,CONTINUE
00258 093A FF02          SMI    2
00259 093C 321F    >     BZ     CK3
```

```
00260 093E 3024  >          BR     CK4       ;FIND FREQ
00261                 ;
00262                 ;
00263 0940 BD         MOREPX GLO    RD        ;DONE??
00264 0941 326B  >           BZ     ALARM     ;DO ALARM
00265 0943 2D                DEC    RD
00266 0944 2E                DEC    RE
00267 0945 2F                DEC    RF
00268 0946 C00RE9  >          LBR    PKM
00269                 ;
00270                 ;
00271 0949 E7         FREQ   SEX    R7        ;OUTPUT FREQ.
00272 094A 62                OUT    2
00273 094B 27                DEC    R7
00274 094C R9                GLO    R9        ;RESET LO,SCN1,
00275 094D FA83              ANI    83H       ;SCN SW. BITS
00276 094F A9                PLO    R9
00277 0950 99                GHI    R9        ;RESET SCN1
00278 0951 FA83              ANI    83H
00279 0953 B9                PHI    R9
00280 0954 E3                SEX    R3
00281 0955 65                OUT    5
00282 0956 02                BYTE   02H
00283 0957 7A         BEEP   REQ              ;BEEP WHEN FINISHED
00284 0958 FFFF              LDI    0FFH
00285 095A BF                PHI    RF
00286 095B 2F         B0     DEC    RF
00287 095C 9F                GHI    RF
00288 095D 3A5B  >           BNZ    B0
00289 095F 7B                SEQ
00290 0960 F820              LDI    20H
00291 0962 BF                PHI    RF
00292 0963 2F         BEEP1  DEC    RF
00293 0964 9F                GHI    RF
00294 0965 3A63  >           BNZ    BEEP1
00295 0967 7A                REQ
00296                 ;
00297 0968 C00F1D  >          LBR    MOKED    ;GO TO WAIT MODE
00298                 ;
00299                 ;......ALARM ROUTINE..........
00300                 ;
00301 096B 7A         ALARM  REQ              ;FLASH LED ON&OFF
00302 096C 3170  >           B0     A1
00303 096E 7B                SEQ
00304 096F 38                SKP
00305 0970 7A         A1     REQ
00306 0971 F820       D9     LDI    20H       ;WAIT AWHILE
00307 0973 BF                PHI    RF
00308 0974 2F         D10    DEC    RF
00309 0975 9F                GHI    RF
00310 0976 3A74  >           BNZ    D10
00311 0978 306C  >           BR     A0
00312                 ;
00313                 ;
00314                 ;......AUTO-BALANCE ROUTINE........
00315                 ;
00316 097A 7B         AUTBAL SEQ              ;LITE LED
00317 097B 34B4  >           B1     DOWN      ;UP OR DOWN?
00318 097D EC         UP     SEX    RC        ;OUTPUT COARSE,
00319 097E 61                OUT    1         ;AND INCREMENT
00320 097F D4                SEP    R4        ;WAIT
00321 0980 F9EA  >           WORD   DELTA
00322 0982 3C7D  >           BN1    UP        ;REPEAT IF NEC.
00323 0984 EC         DOWN   SEX    RC        ;OUTPUT COARSE,
00324 0985 61                OUT    1         ;AND DECREMENT
00325 0986 2C                DEC    RC
```

```
00326 0987 2C               DEC    RC
00327 0988 D4               SEP    R4       ;WAIT
00328 0989 09EA      >      LBRD   DELTA
00329 098B 34B4      >      B1     DOWN     ;NOT DONE
00330 098D C4               NOP
00331 098E C4               NOP
00332 098F C4               NOP
00333 0990 EB        FINE   SEX    RB       ;OUTPUT FINE
00334 0991 67               OUT    7        ;AND INCREMENT
00335 0992 D4               SEP    R4       ;WAIT
00336 0993 09EA      >      LBRD   DELTA
00337 0995 349E      >      B1     EXITB    ;IF PASSED,FINISHED
00338 0997 8B               GLO    RB       ;ELSE IS FINE=0?
00339 0998 3A90      >      BNZ    FINE     ;NO,REPEAT
00340 099A EC               SEX    RC       ;YES,OUTPUT
00341 099B 61               OUT    1        ;AND INC. COARSE
00342 099C 3090      >      BR     FINE     ;THEN REPEAT
00343 099E 89        EXITB  GLO    R9       ;RESET BAL.SW.
00344 099F FA8F             ANI    8FH
00345 09A1 A9               PLO    R9
00346 09A2 7A               REQ             ;SHUT-OFF LED
00347 09A3 C009B1D   >      LBR    MORED    ;GO DISPLAY
00348                       ;
00349                       ;......INTERRUPT SERVICE ROUTINE.......
00350                       ;
00351 09A6 70        EXITI  RET
00352 09A7 22        ISR    DEC    R2       ;SAVE <X>
00353 09A8 78               SAV
00354 09A9 22               DEC    R2
00355 09AA 73               STXD
00356 09AB 76               SHRC
00357 09AC 73               STXD            ;D&DF
00358 09AD 9F               GHI    RF
00359 09AE 73               STXD
00360 09AF 8F               GLO    RF
00361 09B0 73               STXD 00362 09B1 F880             LDI    80H      ;WAIT FOR DEBOUNCE
00363 09B3 BF               PHI    RF
00364 09B4 2F        D1     DEC    RF
00365 09B5 8F               GLO    RF
00366 09B6 CA09B4    >      LBNZ   D1
00367                       ;
00368 09B9 F881             LDI    81H      ;POINT <X>
00369 09BB BF               PHI    RF
00370 09BC F800             LDI    0        ;TO "SAFE" AREA
00371 09BE AF               PLO    RF
00372 09BF EF               SEX    RF
00373 09C0 6E               INP    6        ;GET SWITCHES
00374 09C1 A9               PLO    R9
00375 09C2 E2        ASLEEP SEX    R2       ;RESET X
00376 09C3 12               INC    R2
00377 09C4 42               LDA    R2
00378 09C5 BF               PHI    RF       ;RESTORE:
00379 09C6 42               LDA    R2
00380 09C7 AF               PLO    RF       ;RF
00381 09C8 42               LDA    R2
00382 09C9 FE               SHL
00383 09CA 42               LDA    R2       ;DF&D
00384 09CB FC08             LDI    HI(LOOK)          ;RUN AT LOOK
00385 09CD B3               PHI    R3       ;AFTER INTERRUPTS
00386 09CE FB34             LDI    LO(LOOK)
00387 09D0 A3               PLO    R3
00388 09D1 C009A6    >      LBR    EXITI    ;ESCAPE
00389                       ;
00390                       ;
```

```
00391                    ;........A TO D CONVERSION SUBROUTINE.........
00392                    ;
00393                    ;
00394 09D4 34DD     >   A10D   B1     ADWN        ;UP OR DOWN FIRST?
00395 09D6 EC           AUP    SEX    RC          ;OUTPUT COARSE
00396 09D7 61                  OUT    1           ;TO D-A&INC.
00397 09D8 D4                  SEP    R4          ;WAIT FOR DATA
00398 09D9 09F1     >          WORD   PAUSE       ;TO SETTLE
00399 09DB 3CD6     >          BN1    AUP         ;MORE IF NEC.
00400                    ;
00401 09DD EC           ADWN   SEX    RC          ;OUTPUT COARSE
00402 09DE 61                  OUT    1           ;TO D-A&DEC.
00403 09DF 2C                  DEC    RC
00404 09E0 2C                  DEC    RC
00405 09E1 D4                  SEP    R4          ;WAIT FOR DATA
00406 09E2 09F1     >          WORD   PAUSE       ;TO SETTLE
00407 09E4 3CE9     >          BN1    EXXIT
00408 09E6 C009DD   >          LBR    ADWN
00409 09E9 D5           EXXIT  SEP    R5          ;RETURN
00410                    ;
00411                    ;
00412                    ;
00413                    ;........TIME DELAY SUBROUTINE........
00414                    ;
00415 09EA F880         DELTA  LDI    80H         ;WASTE TIME
00416 09EC AF                  PLO    RF
00417 09ED 2F           D2     DEC    RF
00418 09EE 8F                  GLO    RF
00419 09EF 3AED     >          BNZ    D2
00420 09F1 D5           PAUSE  SEP    R5          ;RETURN
00421                    ;
00422                           END   SECTION
TEKTRONIX         1802 ASM V3.3  SYMBOL TABLE                      PAGE   10

SCALARS

DATA1 -- 0200         DATA2 -- 0300         FREE --- 8C00
    R0 ----- 0000         R1 ----- 0001         R2 ----- 0002
    R3 ----- 0003         R4 ----- 0004         R5 ----- 0005
    R6 ----- 0006         R7 ----- 0007         R8 ----- 0008
    R9 ----- 0009         RA ----- 000A         RB ----- 000B
    RC ----- 000C         RD ----- 000D         RE ----- 000E
    RF ----- 000F

ED520 SECTION (09F2)

A0 ----- 096C         A1 ----- 0970         ADWN --- 09DD
    ALARM -- 096B         ASLEEP - 09C2         A10D --- 09D4
    AUP ---- 09D6         AUTBAL - 097A         B0 ----- 095B
    BEEP --- 0957         BEEP1 -- 0963         CK0 ---- 0912
    CK1 ---- 0930         CK2 ---- 091D         CK3 ---- 091F
    CK4 ---- 0924         CKOSCK - 08FF         D1 ----- 09E4
    D10 ---- 0974         D2 ----- 09ED         D9 ----- 0971
    DELTA -- 09EA         DISP --- 0821         DOWN --- 0984
    ENDSCN - 08A9         EX11B -- 099E         EX111 -- 09A6
    EXXIT -- 09E9         FIVE --- 0990         FREQ --- 0949
    ISR ---- 09A7         L1 ----- 08D2         L2 ----- 08C1
    LOFF --- 08DB         LOOK --- 0834         MAIN --- 0800
    MANUAL - 083F         MORED -- 081D         MOREPK - 0940
    PAUSE -- 09F1         PK0 ---- 09E9         SCAN1 -- 0855
    SCAN10 - 085C         SCAN11 - 0868         SCAN2 -- 0882
    SCAN20 - 0889         SCAN21 - 0895         SCNCHK - 084B
    SORT --- 08AE         UP ----- 097D
```

It will be understood that modifications and variations may be effected without departing from the spirit and scope of the novel concepts of this invention.

We claim:

1. In a nondestructive testing system including measuring means for developing an output signal corresponding to characteristics of a structure under test, said measuring means including adjustable means for controlling the value of a test parameter over a certain range, and set-up means for adjusting said adjustable means, said set-up means comprising: memory means for storage of the value of said output signal and the concurrent value of said test parameter, program means for control of said adjustable means and said memory means, said program means being operable under each of a plurality of different set-up test conditions for adjusting the value of said test parameter over said certain range and for simultaneously storing a set of output signal values and concurrent test parameter values, and comparison means associated with said memory means for comparing said sets of stored output signal and test parameter values and for developing and storing an optimum parameter value at which a predetermined correspondence between output signals is obtained during said plurality of different set-up test conditions, and means operative upon storage of said optimum parameter value for then adjusting said adjustable means to obtain said optimum test parameter value during subsequent operation of the said system in testing structures of unknown characteristics.

2. In a nondestructive testing system as defined in claim 1 for developing an output signal which is a function of a first characteristic of a structure under test while being unaffected by a second characteristic of the structure under test, said second characteristic having one value in a first of said set-up test conditions and having a substantially different value in a second of said set-up test conditions, and said comparison means being operable to develop and store an optimum parameter value at which said output signals during said first and second set-up test conditions are equal.

3. In a nondestructive testing system as defined in claim 2 including an eddy current probe arranged to be placed in proximity to a portion of a metal part, one of said first and said second characteristics being the conductivity of said metal parts and the other of said first and second characteristics being the spatial relationship between said probe and said metal part.

4. In a nondestructive testing system as defined in claim 3, said first characteristic being the conductivity of said metal part.

5. In a nondestructive testing system as defined in claim 1 including an eddy current probe and oscillator means for supplying a variable frequency drive signal to said probe, said adjustable means being arranged for controlling the frequency of said oscillator means.

6. In a nondestructive testing system as defined in claim 5, said oscillator means being a voltage-controlled oscillator, and said adjustable means including a digital-to-analog converter for supplying a variable voltage to said oscillator means controlled by digital signals applied thereto.

7. In a nondestructive testing system as defined in claim 6, means for developing digital data corresponding to said output signal values.

8. In a nondestructive testing system as defined in claim 7, microcomputer means for applying digital control signals to said digital-to-analog converter means and including said memory means, said memory means being effective for storing said digital data corresponding to said output signal values, and said microcomputer means further including said comparison means.

9. In a nondestructive testing system as defined in claim 1 for sorting of parts having one or the other of two characteristics, a first of said set-up test conditions being performed with a sample part having one of said characteristics and a second of said set-up test conditions being performed with a part having the other of said characteristics, and said comparison means being operative for storing an optimum parameter value at which a maximum difference is obtained between output signals produced during said first and second set-up test conditions.

10. In a nondestructive testing system as defined in claim 1, balance means operative for producing a predetermined output signal under any selected operating condition.

11. In a nondestructive testing system as defined in claim 10, said balance means being operative during the adjustment of the value of said test parameter over said certain range for determining the value of a balancing signal required to produce a balance at each value of said test parameter, and said program means being operable to store in said memory means the values of said balance signals.

12. In a nondestructive testing system as defined in claim 1, said program means being operable in each of said different set-up test conditions to change the value of said test parameter in progressive steps from one end of said certain range to the other end thereof, said memory means being operable to store digital data corresponding to the value of said output signal at each step of said test parameter, and said comparison means being operable to compare the stored digital data produced during said different set-up test conditions.

13. In a nondestructive testing system as defined in claim 12 for developing an output signal which is a function of a first characteristic of a structure under test while being unaffected by a second characteristic of the structure under test, said set-up test conditions being such that said first characteristic is the same in both first and second set-up test conditions while said second characteristic is substantially different, and said comparison means being operable to develop and store a parameter value at which said stored digital data are substantially equal.

14. In a nondestructive testing system as defined in claim 13, said comparison means being operable to compare said stored data in progressive steps correlated to the progressive steps of change in value of said test parameter and being operable to develop, store and average the first and last parameter values at which said stored digital data are equal.

* * * * *